T 864007

DEFENSIVE PUBLICATION

UNITED STATES PATENT OFFICE

Published at the request of the applicant or owner in accordance with the Notice of Apr. 11, 1968, 849 O.G. 1221. Identification is by serial number of the application and the heading indicates the number of pages of specification, including claims, and of sheets of drawing contained in the application as originally filed. The file of this application is available to the public for inspection; reproduction may be purchased for 30 cents per sheet.

Applications published under the Defensive Publication Program have not been examined as to the merits of alleged invention. The Patent Office makes no assertion as to the novelty of the disclosed subject matter.

PUBLISHED JULY 15, 1969

864 O.G. 730

782,452

PROCESS FOR PREPARING UNSATURATED CARBOXYLIC ACIDS AND ALDEHYDES

Warren E. Campbell, P.O. Box 511, Kingsport, Tenn. 37662

Filed Dec. 9, 1968. Published July 15, 1969
Int. Cl. C07c *57/04;* B01j *11/32;* C07b *3/00*
U.S. Cl. 260—533
No Drawing. 8 Pages Specification

Olefins having 3 to 5 carbon atoms may be oxidized to the corresponding unsaturated acids or aldehydes in the presence of a gas containing molecular oxygen at elevated temperatures using a catalyst comprising a tellurium compound, an oxide of molybdenum, and either an oxide of niobium or tantalum. The tellurium compound is preferably the oxide or a compound containing the oxide equivalent.